(12) United States Patent
Davis et al.

(10) Patent No.: US 11,304,606 B2
(45) Date of Patent: Apr. 19, 2022

(54) METHOD AND SYSTEM FOR ENHANCING RF ENERGY DELIVERY DURING THERMOACOUSTIC IMAGING

(71) Applicant: ENDRA Life Sciences Inc., Ann Arbor, MI (US)

(72) Inventors: Christopher Nelson Davis, Ann Arbor, MI (US); Jang Hwan Cho, Ann Arbor, MI (US); Paul A. Picot, London (CA); Michael M. Thornton, London (CA)

(73) Assignee: ENDRA Life Sciences Inc., Ann Arbor, MI (US)

( * ) Notice: Subject to any disclaimer, the term of this patent is extended or adjusted under 35 U.S.C. 154(b) by 400 days.

(21) Appl. No.: 16/182,650

(22) Filed: Nov. 7, 2018

(65) Prior Publication Data

US 2020/0138298 A1    May 7, 2020

(51) Int. Cl.
    *A61B 5/00*    (2006.01)
    *A61B 5/20*    (2006.01)
    *A61B 5/02*    (2006.01)

(52) U.S. Cl.
    CPC ........ *A61B 5/0093* (2013.01); *A61B 5/02007* (2013.01); *A61B 5/201* (2013.01); *A61B 5/4244* (2013.01); *A61B 5/4872* (2013.01)

(58) Field of Classification Search
    CPC ... A61B 5/0093; A61B 5/4872; A61B 5/4244; A61B 5/201; A61B 5/02007; A61B 2017/00221; A61B 5/4519; A61B 8/4416; A61B 5/0095; A61B 8/08; A61B 8/14; A61B 8/469; A61B 8/5207; A61B 8/5223
See application file for complete search history.

(56) References Cited

U.S. PATENT DOCUMENTS

| 9,888,879 B1 | 2/2018 | Cho et al. |
| 9,888,880 B1 | 2/2018 | Cho et al. |
| 9,980,677 B1 | 5/2018 | Cho et al. |

(Continued)

OTHER PUBLICATIONS

Xiong Wang et al., "Microwave-Induced Thermoacoustic Imaging Model for Potential Breast Cancer Detection", Oct. 2012, IEEE Transactions on Biomedical Engineering, vol. 59, No. 10, 2782-2791 (Year: 2012).*

(Continued)

*Primary Examiner* — Patricia J Park
*Assistant Examiner* — Adil Partap S Virk
(74) *Attorney, Agent, or Firm* — Stanley E. Jelic

(57) ABSTRACT

A method and system for enhancing radio frequency energy delivery to a tissue region of interest. The method and system direct with a radio frequency (RF) applicator, one or more RF energy pulses into the tissue region of interest, the tissue region of interest comprising an object of interest and at least one reference that are separated by at least one boundary; detect with an acoustic receiver, at least one bipolar acoustic signal generated in the tissue region of interest in response to the RF energy pulses and processing the at least one bipolar acoustic signal to determine a peak-to-peak amplitude thereof; adjust the RF applicator to maximize the peak-to-peak amplitude of bipolar acoustic signals generated in the tissue region of interest in response to RF energy pulses generated by the adjusted RF applicator; and direct with the adjusted RF applicator, one or more RF energy pulses into the region of interest.

17 Claims, 10 Drawing Sheets

(56) References Cited

U.S. PATENT DOCUMENTS

2011/0261180 A1* 10/2011 Simon ................. H04N 5/30
 348/77
2019/0216541 A1* 7/2019 Hancock ............ A61B 18/1815

OTHER PUBLICATIONS

Manojit Pramanik et al., "Thermoacoustic and Photoacoustic Sensing of Temperature", Oct. 2009, Journal of Biomedical Optics, vol. 14(5) (Year: 2009).*

Daniel Bauer et al., "Thermoacoustic Imaging and Spectroscopy for Enhanced Breast Cancer Detection", 2011 IEEE International Ultrasonics Symposium Proceedings (Year: 2011).*

Shane Thomas; PCT International Search Report and Written Opinion; dated Jan. 27, 2020; 7 pages total; WIPO; Alexandria, VA, United States.

* cited by examiner

METHOD AND SYSTEM FOR ENHANCING RF ENERGY DELIVERY DURING THERMOACOUSTIC IMAGING

FIELD

The subject disclosure relates to thermoacoustic imaging and in particular, to a method and system for enhancing radio frequency (RF) energy delivery during thermoacoustic imaging.

BACKGROUND

Thermoacoustic imaging is an imaging modality that provides information relating to the thermoelastic properties of tissue. Thermoacoustic imaging uses short pulses of electromagnetic energy, such as, radio frequency (RF) pulses, directed into a subject to heat absorbing features within the subject rapidly, which in turn induces acoustic pressure waves that are detected using acoustic receivers such as one or more thermoacoustic or ultrasound transducer arrays. The detected acoustic pressure waves are analyzed through signal processing, and processed for presentation as thermoacoustic images that can be interpreted by an operator.

In order to direct RF pulses into the subject during thermoacoustic imaging, a radio frequency (RF) applicator is coupled to tissue adjacent a region of interest (ROI) within the subject to be imaged. Sub-optimal coupling of the RF applicator to the tissue may cause issues such as inefficient energy transfer, reduced heating rates, reduced signal intensity, non-uniform energy deposition, tissue hotspots, tissue overheating, RF power supply damage, and poor image quality. Factors that lead to sub-optimal coupling of the RF applicator to the tissue include variability in the size of the subject, the size of tissue within the subject, the geometry of tissue within the subject, the composition of tissue within the subject, etc.

Although techniques for coupling an RF applicator to tissue have been considered, improvements are desired. It is therefore an object at least to provide a novel method and system for enhancing radio frequency (RF) energy delivery during thermoacoustic imaging.

SUMMARY

It should be appreciated that this Summary is provided to introduce a selection of concepts in a simplified form that are further described below in the Detailed Description. This Summary is not intended to be used to limit the scope of the claimed subject matter.

Accordingly, in one aspect there is provided a method for enhancing radio frequency energy delivery to a tissue region of interest, the method comprising: (i) directing, using a radio frequency (RF) applicator, one or more RF energy pulses into the tissue region of interest, the tissue region of interest comprising an object of interest and at least one reference that are separated by at least one boundary; (ii) detecting, using an acoustic receiver, at least one bipolar acoustic signal generated in the tissue region of interest in response to the RF energy pulses and processing the at least one bipolar acoustic signal to determine a peak-to-peak amplitude thereof; (iii) adjusting the RF applicator to maximize the peak-to-peak amplitude of bipolar acoustic signals generated in the tissue region of interest in response to RF energy pulses generated by the adjusted RF applicator; and (iv) directing, using the adjusted RF applicator, one or more RF energy pulses into the region of interest.

In one or more embodiments, the method further comprises performing thermoacoustic imaging of the tissue region of interest using the adjusted RF applicator. The method may also further comprise determining one or more parameters of the object of interest from the thermoacoustic imaging, such as determining at least one of fractional fat content and temperature.

In one or more embodiments, adjusting the RF applicator comprises at least one of: adjusting a distance between the RF applicator and the tissue region of interest; adjusting an impedance of the RF applicator; adjusting a volume of a waveguide of the RF applicator; and adjusting a temperature within the waveguide of the RF applicator.

In one or more embodiments, the boundary is at a location between at least two, different types of tissue. The two different types of tissue may for example be one of: muscle and fat; a blood vessel and fat; and liver tissue and kidney tissue.

According to another aspect there is provided a system for enhancing radio frequency energy delivery to a tissue region of interest comprising an object of interest and a reference that are separated by at least one boundary, the system comprising: a thermoacoustic imaging system comprising an adjustable radio frequency (RF) applicator configured to emit RF energy pulses into the tissue region of interest and heat tissue therein and an acoustic receiver configured to receive bipolar acoustic signals generated in response to heating of tissue in the tissue region of interest; and one or more processors configured to: process received bipolar acoustic signals during calibration of the RF applicator to determine a setting for the RF applicator that yields acoustic bipolar signals with maximum peak-to-peak amplitudes.

In one of more embodiments, the one or more processors are further configured to: process bipolar acoustic signals received by the acoustic receiver in response to RF energy pulses emitted into the tissue region of interest using the RF applicator when conditioned to the setting to determine one or more parameters of the object of interest, such as at least one of fractional fat content and temperature.

In one or more embodiments, a distance between the RF applicator and the tissue region of interest is adjustable.

In one or more embodiments, the adjustable RF applicator comprises at least one tuning element configured to alter an impedance of a waveguide of the RF applicator.

In one or more embodiments, the adjustable RF applicator comprises a waveguide having an adjustable volume.

In one or more embodiments, the adjustable RF applicator comprises at least one heating element configured to alter a temperature within a waveguide of the RF applicator.

According to another aspect there is provided an adjustable radio frequency applicator comprising: a waveguide; at least one radio frequency (RF) emitter positioned within the waveguide and configured to generate RF energy pulses, the waveguide configured to direct generated RF pulses towards a tissue region of interest; and at least one adjustable feature configured to manipulate a characteristic of the waveguide to adjust a frequency of the directed RF energy pulses.

In one or more embodiments, the at least, one adjustable feature is at least one tuning element that extends into the waveguide, the extent to which the at least one tuning element extends into the waveguide being adjustable to alter the impedance of the waveguide.

In one or more embodiments, the at least one adjustable feature is a volume-adjusting feature configured to adjust the internal volume of the waveguide.

In one or more embodiments, the at least one adjustable feature is at least one heating element configured to alter a temperature within the waveguide.

According to another aspect there is provided a method for enhancing radio frequency energy delivery to a tissue region of interest, the method comprising: (i) directing, using a radio frequency (RF) applicator, one or more RF energy pulses into the tissue region of interest, the tissue region of interest comprising an object of interest and at least one reference that are separated by at least one boundary; (ii) detecting, using an acoustic receiver, at least one bipolar acoustic signal generated in the tissue region of interest in response to the RF energy pulses and processing the at least one bipolar acoustic signal to determine a peak-to-peak amplitude thereof; (iii) adjusting the RF applicator; (iv) directing, using the adjusted RF applicator, one or more RF energy pulses into the region of interest; (v) detecting, using the acoustic receiver, at least one bipolar acoustic signal generated in the tissue region of interest in response to the RF energy, pulses generated by the adjusted RF applicator and processing the at least one, bipolar acoustic signal to determine a peak-to-peak amplitude thereof; (vi) comparing the peak-to-peak amplitude determined at step (v) with a previously determined peak-to-peak amplitude; and (v) repeating steps (iii), (iv) and (v) until the peak-to-peak amplitude of the at least bipolar acoustic signal determined at step (v) is maximized.

BRIEF DESCRIPTION OF THE DRAWINGS embodiments will now be described more fully with reference to the accompanying drawings in which.

DETAILED DESCRIPTION OF THE EMBODIMENTS

The foregoing summary, as well as the following detailed description of certain examples will be better understood when read in conjunction with the appended drawings. As used herein, an element or feature introduced in the singular and preceded by the word "a" or "an" should be understood as not necessarily excluding the plural of the elements or features. Further, references to "one example" or "one embodiment" are not intended to be interpreted as excluding the existence of additional examples or embodiments that also incorporate the described elements or features. Moreover, unless, explicitly stated to the contrary, examples or embodiments "comprising" or "having" or "including" an element or feature or a plurality of elements or features having a particular property may include additional elements or features not having that property. Also, it will be appreciated that the terms "comprises", "has", "includes" means "including but not limited to" and the terms "comprising", "having" and "including" have equivalent meanings.

As used herein, the term "and/or" can include any and all combinations of one or more of the associated listed elements or features.

It will be understood that when an element or feature is referred to as being "on", "attached" to, "connected" to, "coupled" with, "contacting", etc. another element or feature, that element or feature can be directly on, attached to, connected to, coupled with or contacting the other element or feature or intervening elements may also be present. In contrast, when an element or feature is referred to as being, for example, "directly on", "directly attached" to, "directly connected" to, "directly coupled" with or "directly contacting" another element of feature, there are no intervening elements or features present.

It will be understood that spatially relative terms, such as "under", "below", "lower", "over", "above", "upper", "front", "back" and the like, may be used herein for ease of description to describe the relationship of an element or feature to another element or feature as illustrated in the figures. The spatially relative terms can however, encompass different orientations in use or operation in addition to the orientations depicted in the figures.

In the following, a method and system for enhancing radio frequency (RF) energy delivery during thermoacoustic imaging are described. Generally, the method and system utilize an RF applicator to obtain thermoacoustic data of tissue within a region of interest (ROI) of a subject. The thermoacoustic data is analyzed and the RF applicator is adjusted to enhance energy delivery to the tissue.

Figure 1:
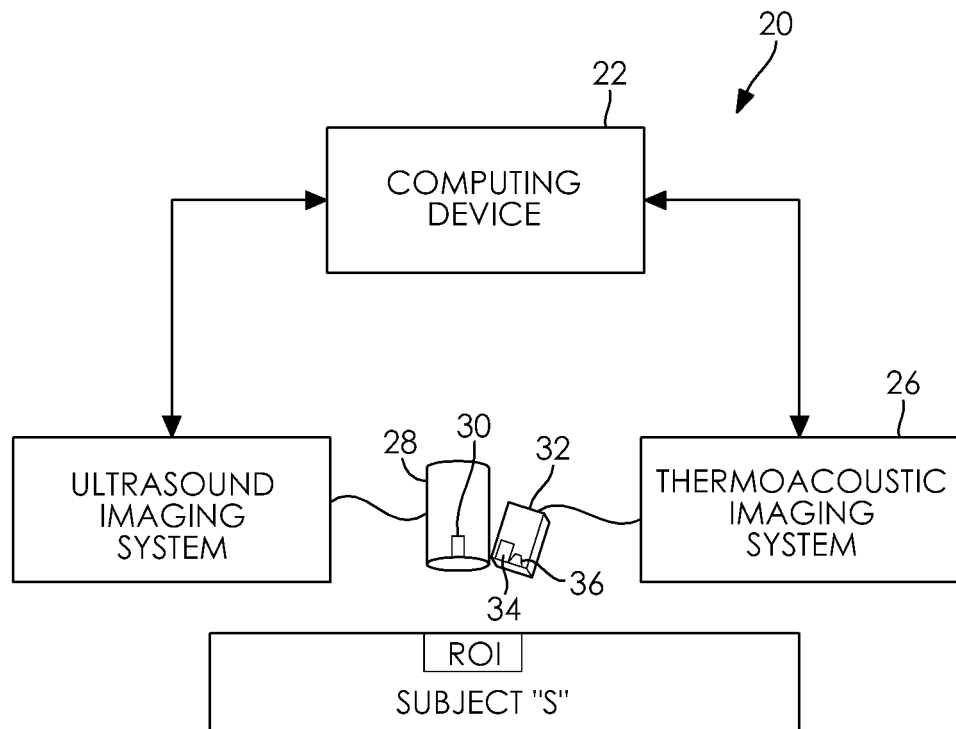
FIG. 1 is a schematic view of an imaging system.

Turning now to FIG. 1, an exemplary imaging system is shown and is generally identified by reference numeral 20. As can be seen, the imaging system 20 comprises a programmed computing device 22 communicatively coupled to an ultrasound imaging system 24 and to a thermoacoustic imaging system 26. The ultrasound imaging system 24 and thermoacoustic imaging system 26 are configured to obtain ultrasound image data and thermoacoustic image data, respectively, of a tissue region of interest ROI associated with a subject S.

The programmed computing device 22 in this embodiment is a personal computer or other suitable processing device comprising, for example, a processing unit comprising one or more processors, system memory (volatile and/or non-volatile memory), other non-removable or removable memory (e.g., a hard disk drive, RAM, ROM, EEPROM, CD-ROM, DVD, flash memory, etc.) and a system bus coupling the various computer components to the processing unit. The computing device 22 may also comprise networking capabilities using Ethernet, Wi-Fi, and/or other suitable network format, to enable connection to shared or remote drives, one or more networked computers, or other networked devices. One or more input devices, such as a mouse and a keyboard (not shown) are coupled to the computing device 22 for receiving operator input. A display device (not shown), such as one or more computer screens or monitors, is coupled to the computing device 22 for displaying one or more generated images that are based on ultrasound image data received from the ultrasound imaging system 24 and/or the thermoacoustic image data received from thermoacoustic imaging system 26.

The ultrasound imaging system 24 comprises an acoustic receiver in the form of an ultrasound transducer 28 that houses one or more ultrasound transducer arrays 30 configured to emit sound waves into the region of interest ROI of the subject S. The sound waves directed into the region of interest ROI of the subject echo off tissue within the region of interest ROI, with different tissues reflecting varying degrees of sound. Echoes that are received by the one or more ultrasound transducer arrays 30 are processed by the ultrasound imaging system 24 before being communicated as ultrasound image data to the computing device 22 for further processing and for presentation as ultrasound images that can be interpreted by an operator. In this embodiment, the ultrasound imaging system 24 utilizes B-mode ultrasound imaging techniques assuming a nominal speed of sound of 1,540 m/s. As ultrasound imaging systems are known in the art, further specifics of the ultrasound imaging system 24 will not be described further herein.

The thermoacoustic imaging system 26 comprises an acoustic receiver in the form of a thermoacoustic transducer 32. The thermoacoustic transducer 32 houses one or more thermoacoustic transducer arrays 34 as well as a radio frequency (RF) applicator 36. It will however be appreciated that the RF applicator 36 may be housed separately from the thermoacoustic transducer 32. The RF applicator 36 is configured to emit short pulses of RF energy that are directed into tissue within the region of interest ROI of the subject. In this embodiment, the RF applicator 36 has a frequency between about 10 Mhz and 100 GHz and has a pulse duration between about 0.1 nanoseconds and 10 nanoseconds. The RF energy pulses delivered to the tissue within the region of interest ROI heat the tissue thereby to induce acoustic pressure waves that are detected by the thermoacoustic transducer 32. The acoustic pressure waves that are detected by the thermoacoustic transducer 32 are processed and communicated as thermoacoustic image data to the computing device 22 for further processing and for presentation as thermoacoustic images that can be interpreted by the operator.

In this embodiment, the ultrasound transducer 28 and thermoacoustic transducer 32 are mechanically interconnected so that the spatial relationship between the one or more ultrasound transducer arrays 30, the one or more thermoacoustic arrays 34 and the RF applicator 36 are known. The spatial relationship is set using a centerline of the one or more ultrasound transducer arrays 34, the one or more thermoacoustic transducer arrays 34, and RF applicator 36. Each centerline is defined as being a mid-point of an area of the respective transduce array.

In this embodiment, the spatial relationship between the one or more ultrasound transducer arrays 30 and the one or more thermoacoustic transducer arrays 34 is such that the centerline of the one or more thermoacoustic transducer arrays 34 is set at know angle α with respect to the centerline (also known as the axial axis or ultrasound transducer array beam axis) of the one or more ultrasound transducer arrays 30. The spatial relationship between the one or more thermoacoustic transducer arrays 34 and the RF applicator 36 is such that the centerline of the RF applicator 36 is spaced-apart and generally parallel to the centerline of the one or more thermoacoustic transducer arrays 34.

The imaging system 20 utilizes the known spatial relationship between the one or more ultrasound transducer arrays 30 and the one or more thermoacoustic transducer arrays 34 to increase the precision and accuracy of thermoacoustic.

The coordinate system of the one or more, ultrasound transducer arrays 30 of the ultrasound transducer 28 and the coordinate system of the one or more thermoacoustic transducer arrays 34 of the thermoacoustic transducer 32 are mapped by the computing device 22 so that acquired ultrasound and thermoacoustic images can be registered. Alternatively, the thermoacoustic imaging system 26 may make use of the one or more ultrasound transducer arrays 30 of the ultrasound transducer 28 by disconnecting the one or more ultrasound transducer arrays 30 from the ultrasound transducer 28 and connecting the one or more ultrasound transducer arrays 30 to the thermoacoustic transducer 32. As will be appreciated, by doing this coordinate mapping between the one or more ultrasound transducer arrays 28 and the one or more thermoacoustic transducer arrays 34 is not required.

Figure 2:
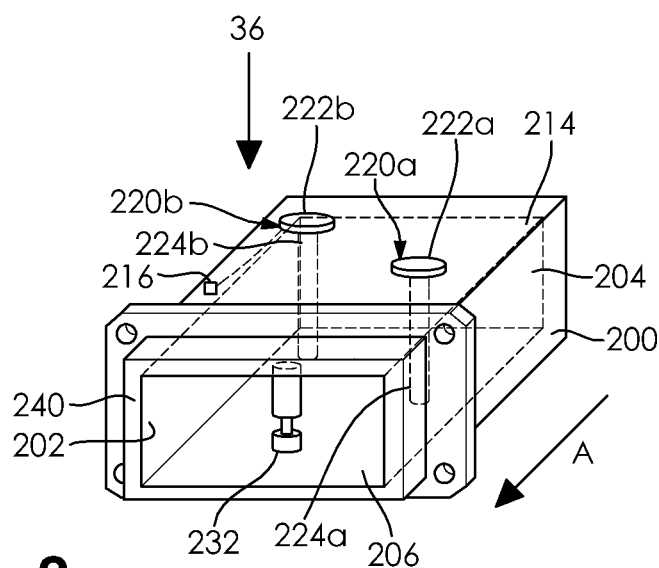
FIGS. 2 and 3 are perspective views of a radio frequency (RF) applicator forming part of the imaging system of FIG. 1.
Figure 3:
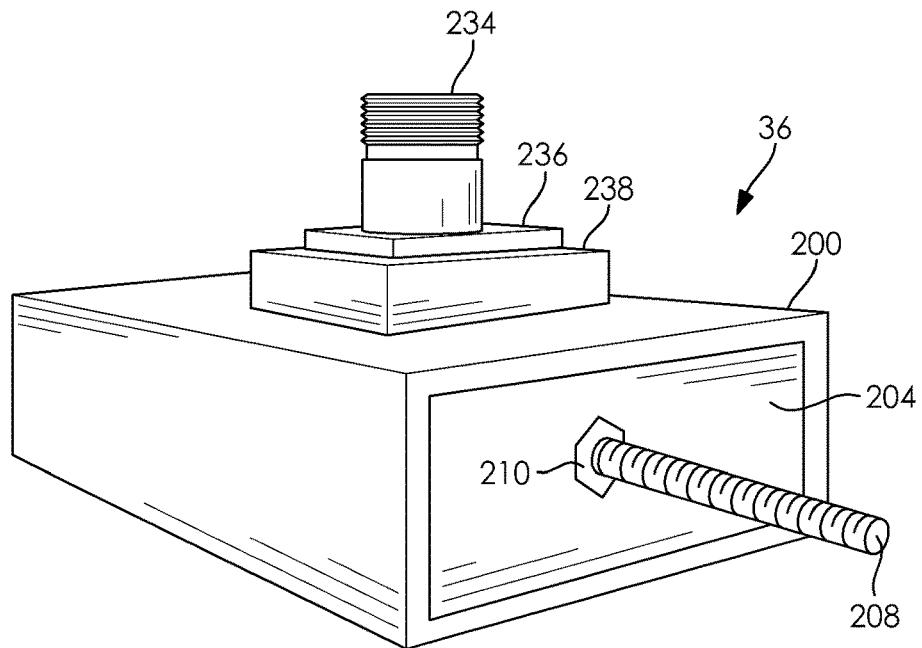
Figure 3A:
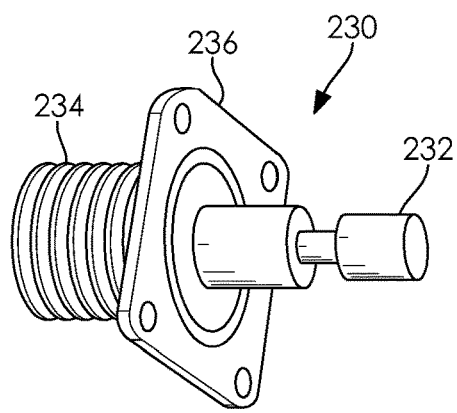
FIG. 3A is a perspective view of an RF source forming part of the RF applicator of FIGS. 2 and 3.

Turning now to FIGS. 2, 3 and 3A, the RF applicator 36 is better illustrated. As can be seen, the RF applicator 36 comprises a hollow, generally rectangular, open-ended housing 200 formed of electrically conductive material. An insert 202 formed of ceramic or other suitable material lines the interior surface of the housing 200. An adjustable backplane 204 is positioned within the insert 202 adjacent one end of the housing 200. The adjustable backplane 204 closes one end of the insert 202 to define a partially enclosed space 206 within the insert 202. In this embodiment, the backplane 204 has a hole therein through which a threaded rod 208 extends. A nut 210 that is affixed to the external major surface of the backplane 204 threadably engages the threaded rod 208. Rotation of the threaded rod 208 causes the nut 210 to travel along the threaded rod 208 and hence, causes the backplane 204 to travel longitudinally within the insert 202. Depending on the direction of rotation of the threaded rod 208, the backplane 204 can be advanced into or out of the insert 202 allowing the volume of the partially enclosed space 206 to be adjusted. Although not shown, a handle may be provided on the threaded rod 208 to facilitate rotation thereof.

Figure 2A:
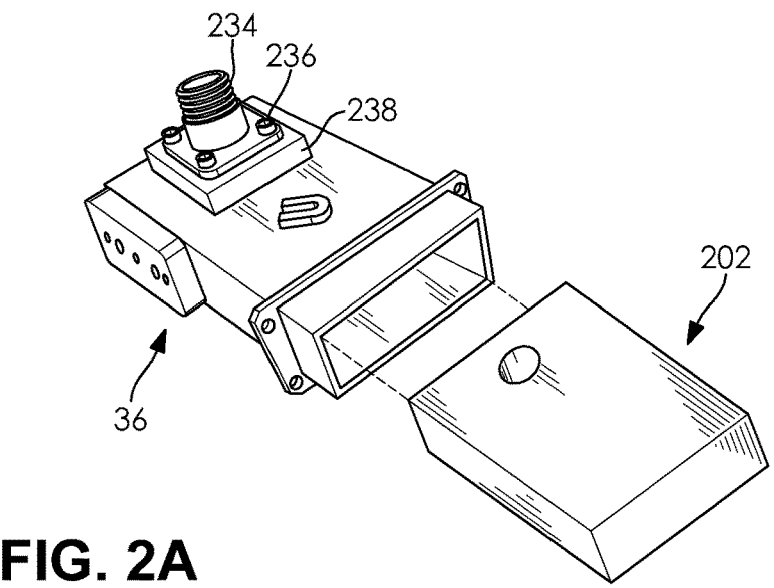
FIG. 2A is a perspective view of a radio frequency (RF) applicator with an insert removed.

FIG. 2A is a perspective view of a radio frequency (RF) applicator with an insert removed. Shown are insert 202, a threaded connector 234 to which control electronics are connected, a flange 236 that overlies a plinth 238, and RF applicator 36.

A heating element 214 and a temperature sensor 216 are accommodated in the space between the outer and inner surfaces of the housing 200. The temperature sensor 216 is configured to communicate temperature data to the computing device 22 indicating the temperature within the partially enclosed space 206 of the insert 202. The heating element 208 is configured to receive control signals from the computing device 22 and is energized when the temperature within the partially enclosed space 206 falls below a set threshold. In this manner, the temperature within the partially enclosed space 206 can be effectively controlled by the computing device 22 by comparing the temperature data received from the temperature sensor 216 with the set temperature and energizing the heating element 214 when needed.

In this embodiment, the heating element 214 extends along a lengthwise edge of the insert 202. Those of skill in the art will however appreciate that variations are possible. The heating element 214 may of course be positioned within the space between the outer and inner surfaces of the housing 200 at alternative locations. Furthermore, multiple heating elements 214 at various positions in the space between the outer and inner surfaces of the housing 200 may be employed. In this embodiment, the temperature sensor 216 is positioned adjacent a lengthwise edge of the insert 202 opposite the heating element 214. The temperature sensor 216 may of course be positioned in the space between the outer and inner surfaces of the housing 200 at alternative locations. Furthermore, multiple temperature sensors 216 at various positions in the space between the outer and inner surfaces of the housing 200 may be employed.

In this embodiment, the RF applicator 36 further comprises a plurality of tuning elements 220a and 220b that are laterally and longitudinally spaced along the housing 200. Tuning element 220a is generally centered along the housing 200 and comprises a head 222a and a threaded rod 224a extending therefrom. Tuning element 220b is to one side and behind the tuning element 220a in the view of FIG. 2 and comprises a head 222b and a threaded rod 224b extending therefrom. The heads 222a and 222b of the tuning elements are in the form of discs and are positioned external of the housing 200 adjacent one of its major surfaces. The threaded rods 222a and 222b of the tuning elements pass through threaded holes in the housing 200 that are aligned with hales in the insert 202 and extend into the partially enclosed, space 206 of the insert 202. Each tuning element 220a, 220b is adjustable by rotating the respective head of the tuning element in a clockwise or counter-clockwise direction to increase or decrease the extent into which the threaded rod extends into the partially enclosed space 206. Although two tuning elements are shown, those of skill in the art will appreciate that the RF applicator 36 may comprise a single tuning element of more than two tuning elements.

An RF source 230 having an RF emitter 232 at one end that is configured to generate RF energy pulses, extends through aligned holes in the housing 200 and insert 202 so that the RF emitter 232 is suspended within the partially enclosed space 206 of the insert 202. The RF source 230 further comprises a threaded connector 234 to which control electronics are connected and a flange 236 that overlies a plinth 238 formed on the housing 200 and through which threaded fasteners pass and engage the plinth 238 thereby to secure the RF source 230 to the housing 200.

A window 240 is positioned at the open end of the housing 200 and insert 202. In this embodiment, the window 240 is in the form of a dielectric stand-off and is configured to permit RF energy pulses emitted by the RF emitter 232 to travel therethrough and exit the RF applicator 36.

During operation of the RF applicator 36, the RF emitter 232 of the RF source 230 is conditioned to generate short pulses of RF energy into the partially enclosed space 206 of the insert 202. The housing 200 and insert 202, which function as a waveguide, confine and direct the emitted RF energy pulses so that the RF energy pulses travel along and then out of the RF applicator 36 through the window 240 in the direction indicated by arrow A. Once the RF energy pulses travel out of the RF applicator 36 through the window 210, they are directed into the subject to deliver energy to tissue within the region of interest ROI of the subject S.

During operation of the RF applicator 36, the frequency of the RF energy pulses can be varied in a number of ways. For example, using one or more of the tuning elements 220a, 220b, the RF applicator 36 can be tuned by inserting more or less threaded rod into the partially enclosed space 206 of the insert 202 to alter the impedance of the waveguide. When a tuning element 220a, 220b is adjusted such, that only a small amount of its threaded rod extends into the partially enclosed space 206, the tuning element 220a, 220b acts as a shunt capacitor. As the tuning element 220a, 220b is adjusted to increase the amount of threaded rod that extends into the partially enclosed space 206, the capacitance increases. When the tuning element 220a, 220b has been adjusted such that the amount of threaded 201 rod that extends into the partially enclosed space 206 is greater than one-quarter of the wavelength within the waveguide defined by the housing 200 and insert 202, the tuning element 220a, 220b resonates equivalent to a series LC circuit. Further increasing the amount of threaded rod that extends into the partially enclosed space 206 of the insert 202 causes the impedance to change from capacitive to inductive.

Alternatively or in addition to, the frequency of the RF energy pulses emitted by the RF applicator 36 can be adjusted by changing the temperature within the partially enclosed space 206 of the insert 202. In particular, by increasing the temperature of the partially enclosed space 206 within the insert 202 using the heating element 214 and temperature sensor 216, the frequency of the RF energy pulses emitted by the RF applicator 36 can be increased. By decreasing the temperature of the partially enclosed space 206 within the insert 202, the frequency of the RF energy pulses emitted by the RF applicator 36 can be decreased.

Alternatively or in addition to, the frequency of the RF energy pulses emitted by the RF applicator 36 may be tuned or adjusted by moving the backplane 204 thereby to change the volume of the partially enclosed space 206 of the insert 202. As will be described, adjusting the frequency of the RF energy pulses can help to enhance energy delivery during thermoacoustic imaging.

Thermoacoustic imaging can be used to contrast fat or fatty tissues with soft or lean tissues due to their lower electrical conductivity and permittivity in RF compared to other water and ion-rich soft or lean tissues. Fat and fatty tissues also have a lower absorption coefficient compared to soft or lean tissues like muscle. As such, during thermoacoustic imaging of a region of interest that includes a boundary between fat or fatty tissue and soft or lean tissue, bipolar acoustic signals are generated that are received by the thermoacoustic transducer 32. This is due to the fact that the soft or lean tissue absorbs more heat than the fat or fatty tissue causing it to expand rapidly across the boundary and into the fat or fatty tissue, that expands less, and then quickly contract. The strength or peak-to-peak values of the bipolar acoustic signals depend on the relative absorption properties of the fat or fatty tissue and the soft or lean tissue.

Figure 4:
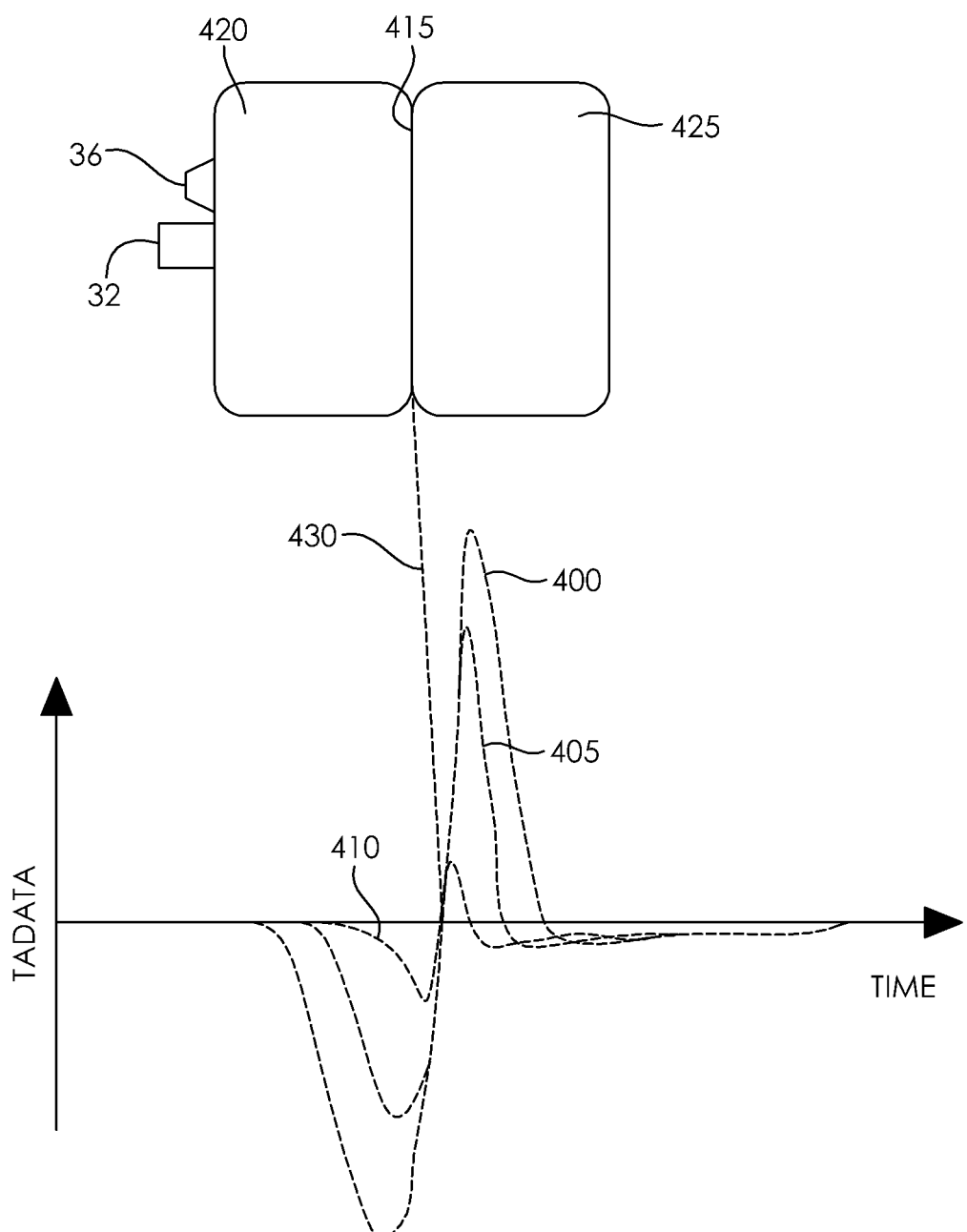
FIG. 4 is a graph showing exemplary bipolar acoustic signals.

Exemplary bipolar acoustic signals 400, 405, and 410 are shown in FIG. 4. The bipolar acoustic signals 400, 405, and 410 are generated in response to thermoacoustic imaging of a tissue region of interest ROI comprising a first tissue 420 and a different type of second tissue 425 that are separated by a boundary 415. The dashed line 430 indicates a time point corresponding to the boundary 415. The peak-to-peak amplitude of each bipolar acoustic signal 400, 405, and 410 is proportional to a difference in the absorption coefficients of the first tissue 420 and second tissue 425. In FIG. 4, the first tissue 420 is a kidney and has no fat. For bipolar acoustic signal 400, the second tissue 425 is a fatty liver that has a high fractional fat content. For bipolar acoustic signal 405, the second tissue 425 is an unhealthy liver that has a medium fractional fat content. For bipolar acoustic signal 410, the second tissue 425 is a healthy liver that has a low fractional fat content. As can be seen, the peak-to-peak value of bipolar acoustic signal 400 is greater than that of bipolar acoustic signals 405, 410, and the peak-to-peak value of bipolar acoustic signal 405 is greater than that of bipolar acoustic signal 410. The differences in the peak-to-peak values of the bipolar acoustic signals 400, 405, and 410 represent the extent to which the first tissue 420 expands into the boundary 415 and into the second tissue 425 before contracting.

Different tissues have characteristic dielectric properties at particular frequencies. The dielectric properties determine how much energy is absorbed by tissue. When RF energy pulses are transmitted through tissue, the RF energy pulses are attenuated. The amount of attenuation can be determined using the dielectric properties of the tissue and the physical properties of the tissue. Fatty tissue absorbs less energy than lean tissue. As such, fatty tissue attenuates the RF energy pulses less than normal tissue. Using these, properties, the amount of attenuation of tissue can be estimated and this may be used to determine how much fat is in the tissue. As such, adjusting the frequency of the RF energy pulses emitted by the RF applicator 36 can help to enhance energy delivery during thermoacoustic imaging.

Figure 5:
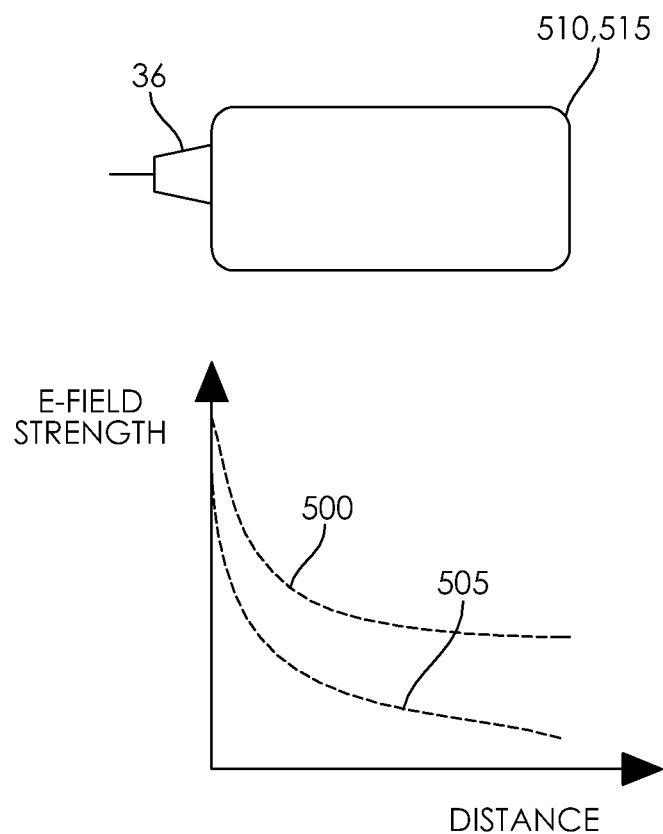
FIG. 5 is a graph showing exemplary electric field strength attenuation curves.

Exemplary electric field strength attenuation curves 500 and 505 are shown in FIG. 5. Each electric field strength attenuation curve 500, 505 represents the electric field strength attenuation of tissue 510, 516, respectively, as a function of distance from the RF applicator 36 of the thermoacoustic imaging system 26. The tissue 510 associated with electric field strength attenuation curve 500 has a higher fat concentration than the tissue 515 associated with electric field strength attenuation curve 505.

Figure 6:
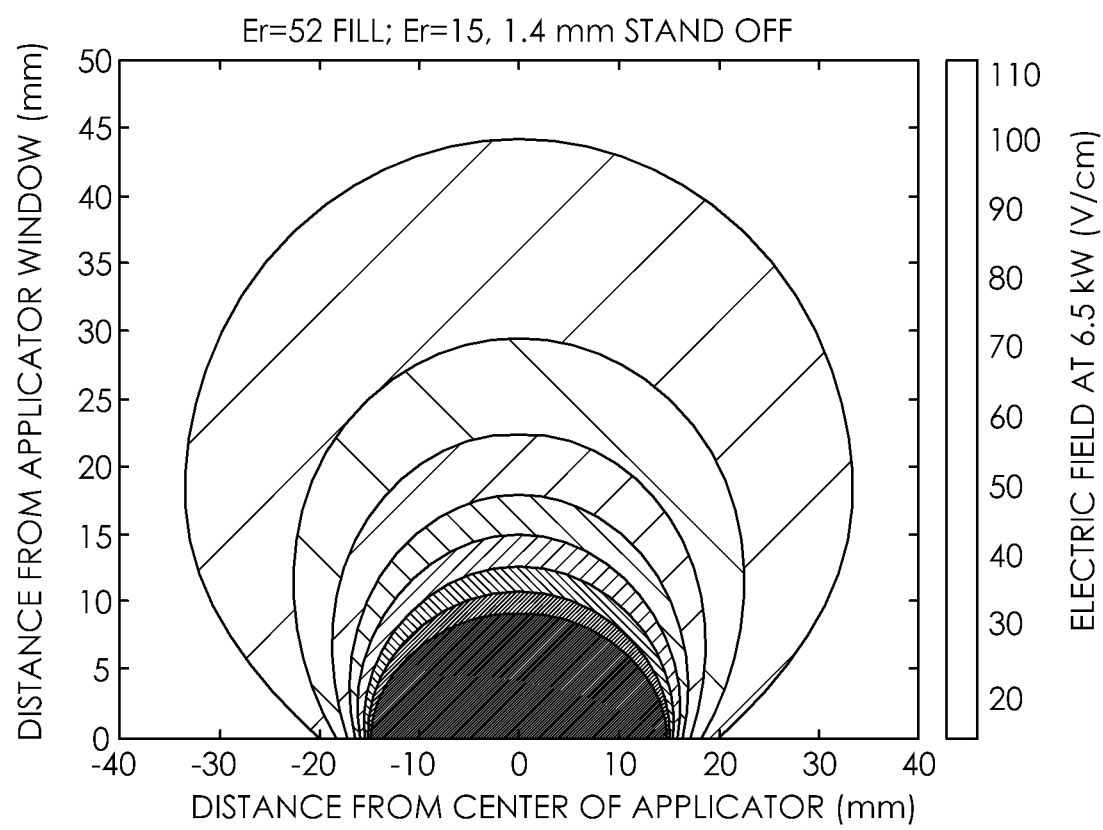
FIG. 6 is a graph showing exemplary flux (energy gradient) of, the RF energy pulses emitted by the RF applicator of FIGS. 2 and 3.

FIG. 6 shows the flux (energy gradient) of an RF energy pulse generated by the RF applicator 36 as it exits the waveguide defined by the housing 200 and insert 202. The window 240 is located and centered at the 0 value of the x-axis. As can be seen, as the distance from the center of the RF applicator 36 increases, the electric field strength decreases. As such, adjusting the distance between the RF applicator 36 and the tissue can help to enhance energy delivery during thermoacoustic imaging.

The imaging system 20 exploits the relationship between the energy absorbing characteristics of the different types of tissue being imaged, the adjustability of the RF applicator 36, and the relationship between the distance between the RF applicator 36 and the tissue to enhance energy delivery during thermoacoustic imaging.

Figure 7:
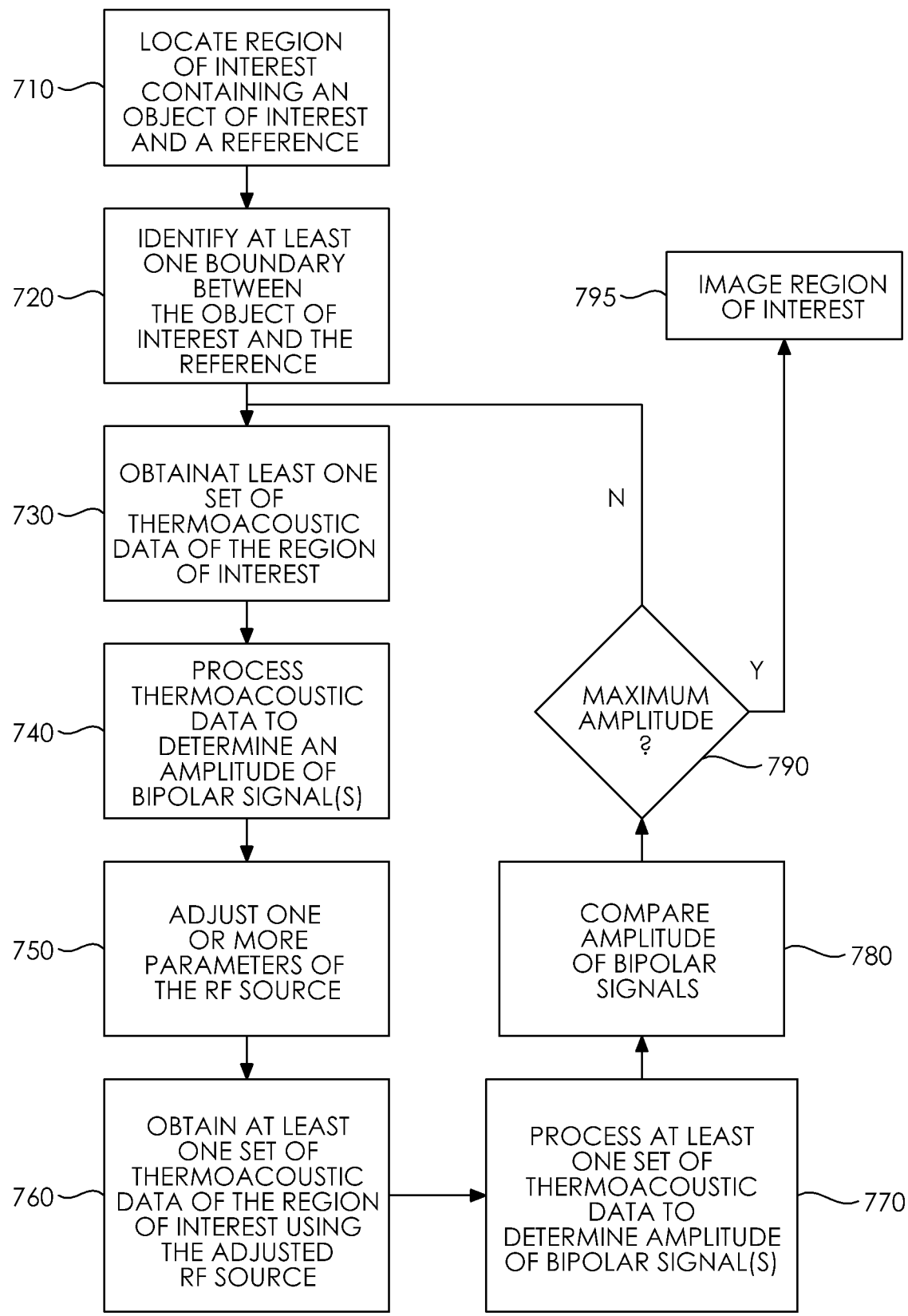
FIG. 7 is a flow chart of a method for enhancing radio frequency delivery during thermoacoustic imaging.

Turning, now to FIG. 7, a method of enhancing RF energy delivery during thermoacoustic imaging is shown. Initially during the method, a region of interest ROI within the subject S to be imaged that contains an object of interest and a reference separated by at least one boundary is located (step 710). In this embodiment, the region of interest ROI is located using the ultrasound imaging system 24. Specifically, ultrasound image data obtained by the ultrasound imaging system 24 is communicated to the computing device 22. The ultrasound image data is processed by the computing device 22 and a reconstructed ultrasound image is presented on the display device. The operator moves the ultrasound transducer 28 on the subject's body until the region of interest is located. When locating the region of interest, the computing, device 22 overlays information associated with the angle of the centerline of the one or more transducer arrays 30 of the ultrasound transducer 28 overtop of the reconstructed ultrasound image on the display device. The information is used to provide feedback to the operator to ensure the axial axis of the ultrasound transducer 28 is generally perpendicular to a boundary between the object of interest and the reference.

Figure 8:
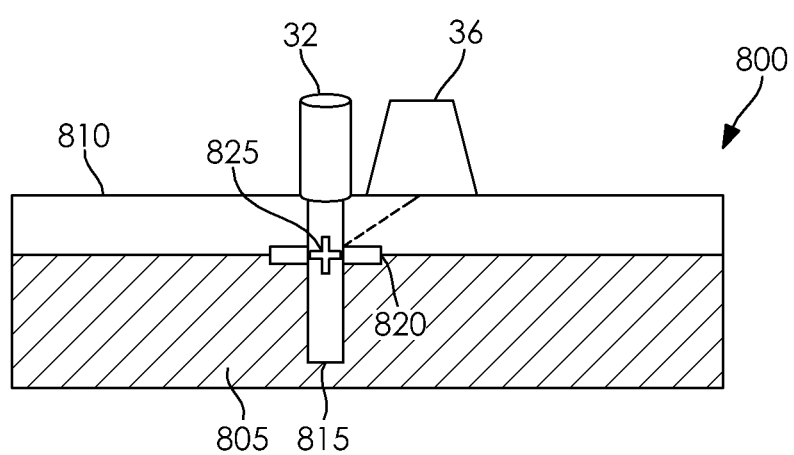
FIG. 8 is an exemplary tissue region of interest containing an object of interest and a reference.

An exemplary region of interest 800 containing an object of interest 805 and a reference 810 is shown in FIG. 8. In this embodiment, the object of interest 805 is the subject's liver and the reference 810 is the subject's kidney. Also shown in FIG. 8 is the RF applicator 36 and the thermoacoustic transducer 32.

At least one boundary between the object of interest and the reference is then identified in the reconstructed ultrasound image (step 720). In this embodiment, the at least one boundary is identified by the operator using an input device such as a mouse coupled to the computing device 22. Specifically, the operator draws a box that encompasses at least a portion of the object of interest 805, at least a portion of the reference 810 and the identified boundary between the portions of the object of interest and the reference. The computing device 22 provides feedback to the operator via the display device to indicate the approximate angle between the box and the boundary to ensure the box is generally perpendicular to the boundary.

An exemplary box 815 is shown in FIG. 8. As can be seen, the box 815 encompasses a portion of the object of interest 805 (the liver), a portion of the reference 810 (the kidney), and the boundary 820 between the object of interest 805 and the reference 810. The boundary 820 is selected at a particular location 825 where the liver and the kidney are in close relation to one another.

An RF applicator calibration is then performed. During the calibration, the RF applicator 36 is conditioned to generate short RF energy pulses. The RF energy pulses travel out of the waveguide defined by the housing 200 and insert 202, through the window 240, and are directed into the region of interest 800 to deliver energy to the object of interest 805 and the reference 810 within the region of interest ROI. In response, bipolar acoustic signals are generated that are detected by the thermoacoustic transducer 32 (step 730).

Since the angle α between the centerline of the one or more transducer arrays 30 of the ultrasound transducer 28 and the centerline of the one or more transducer arrays 34 of the thermoacoustic transducer 32 is known, the operator is able to adjust position of the thermoacoustic transducer 32 with respect to the subject's body such that the thermoacoustic imaging system 26 is able to obtain thermoacoustic image data of the region of interest at a desired imaging angle σ. The desired imaging angle σ is such that the centerline of the one or more transducer arrays 34 of the thermoacoustic transducer 32 extends through the boundary 820 between the object of interest 805 and the reference 810.

Figure 9:
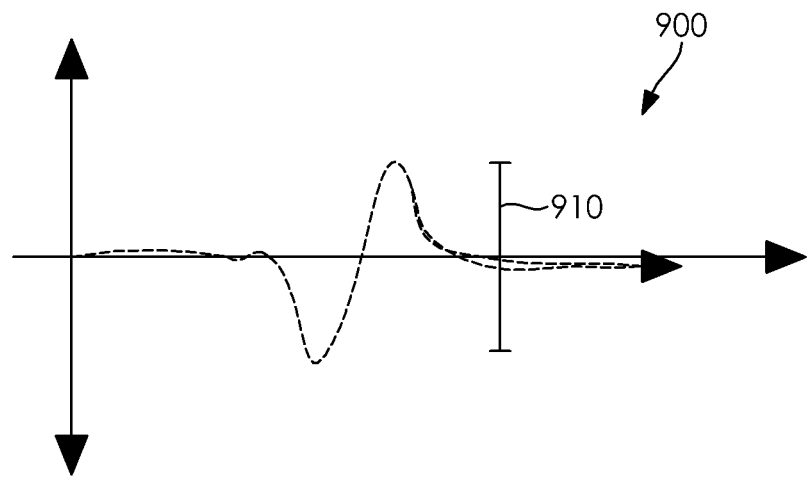
FIGS. 9 to 11 are exemplary bipolar acoustic signals obtained according to the method of FIG. 7.

The bipolar acoustic signals are in turn communicated to the computing device 22 for processing (step 740). In this embodiment, the computing device 22 is programmed to determine the peak-to-peak amplitudes of the bipolar acoustic signals. An exemplary bipolar acoustic signal 900 is shown in FIG. 9. As can be seen, the bipolar acoustic signal 900 comprises a peak-to-peak amplitude 910.

The RF applicator 36 is then adjusted to alter the frequency of the RF energy pulses emitted thereby (step 750). In this embodiment, the RF applicator 36 may be adjusted by rotating one or both of the tuning elements 220*a* and 220*b* to change the impedance of the waveguide, changing the volume of the partially enclosed space 206 of the insert 202 by moving the backplane 204, and/or by increasing or decreasing the temperature within the partially enclosed space 206 of the insert 202. Further, the distance between the RF applicator 36 and the region of interest ROI may be increased or decreased (e.g. by moving the RF applicator to a different location on a patient's skin or pressing the applicator into the subject to compress the subject).

Figure 10:
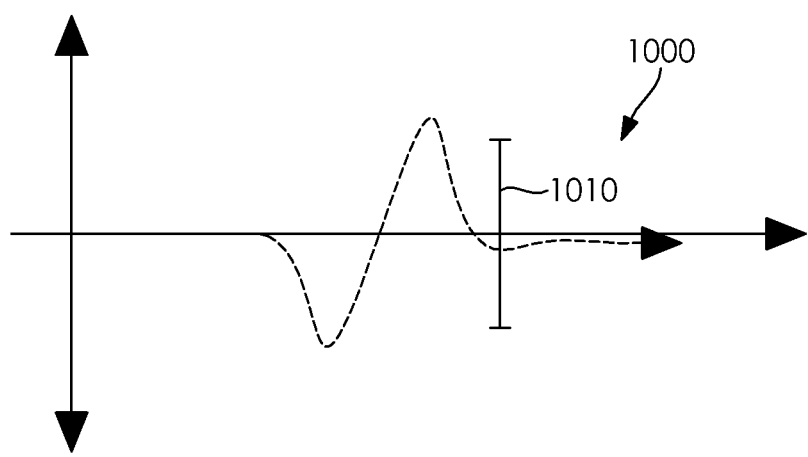

Following the RF applicator adjustment, the RF applicator 30 is again conditioned to generate short RF energy pulses that are directed into the region of interest 800 to deliver energy to the object of interest 805 and the reference 810 (step 760). The resultant bipolar acoustic signals that are generated in the tissue of the region of interest and received by the thermoacoustic transducer 32 are again communicated to the computing device 22 for processing to determine the peak-to-peak amplitudes of the bipolar acoustic signals (step 770). The computing device 22 then compares the peak-to-peak amplitudes of the bipolar acoustic signals with those determined at step 740 to determine if there has been an increase in the peak-to-peak amplitudes (step 780). FIG. 10 shows an exemplary bipolar signal 1000 comprises a peak-to-peak amplitude 1010 that is greater that the peak-to-peak amplitude 910 of bipolar signal 900 (shown in FIG. 9).

Figure 11:
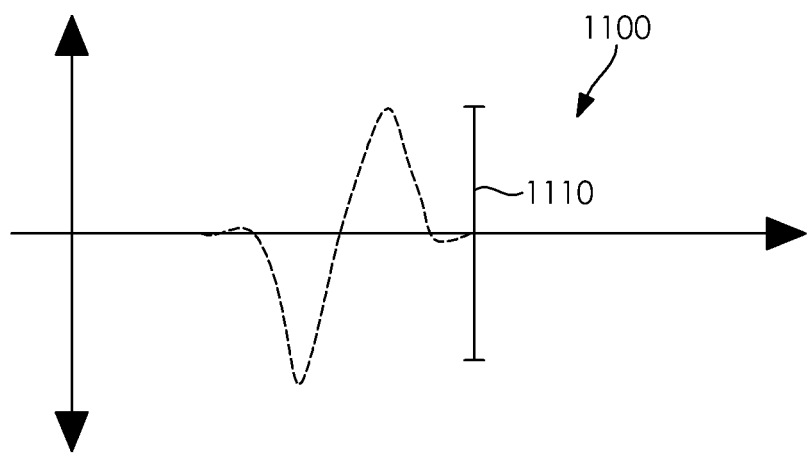

If there is an increase in the peak-to-peak amplitudes, the process reverts back to step 730 and steps 730 to 770 are re-preformed. These steps are preformed iteratively until acoustic bipolar signals having maximum peak-to-peak amplitudes are determined (step 790). FIG. 11 shows an exemplary bipolar acoustic signal 1100 having a maximum peak-to-peak amplitude 1110. As can be seen, the peak-to-peak amplitude 1110 is greater than peak-to-peak amplitude 910 (FIG. 9) and peak-to-peak amplitude 1010 (FIG. 10). At this stage, the RF applicator calibration is deemed complete.

When the RF applicator 36 has been adjusted to maximize the peak-to-peak amplitudes of the generated bipolar acoustic signals, the RF energy delivered to the region of interest ROI is deemed enhanced and the thermoacoustic imaging system 26 is determined to be in condition for carrying out thermoacoustic imaging of the region of interest. Thermoacoustic imaging of the region of interest is then carried out using the adjusted RF applicator 36 and the resultant bipolar acoustic signals that are generated in the tissue of the region of interest and received by the thermoacoustic transducer 32 are communicated to the computing device 22 for processing (step 795). As will be appreciated, when the bipolar acoustic signals have been maximized, imaging results are more accurate. The bipolar acoustic signals are then processed to determine one or more parameters of the object of interest (step 770). For example, the bipolar acoustic signals may be processed to estimate the fractional fat content of the object of interest, as described in U.S. Pat. Nos. 9,888,879, 9,888,880 and 9,980,677, the relevant portions of which are incorporated herein by reference. As will be appreciated, the bipolar acoustic signals can be processed to determine other factors such as for example temperature of tissue.

Those skilled in the art will appreciate that in embodiments the computing device may be programmed to adjust parameters of the RF applicator. For example, the computing device may be coupled to one or more actuators configured to adjust the tuning elements 220a, 220b and/or the threaded rod 308.

Those skilled in the art will appreciate that the above-described method may be performed on a phantom designed to mimic an area of interest. In this embodiment, the RF applicator may be adjusted to maximize the peak-to-peak amplitude of the bipolar acoustic signals prior to imaging a patient. Further, the method may be performed on numerous phantoms of various sizes to mimic different sizes of patients.

Figure 12:
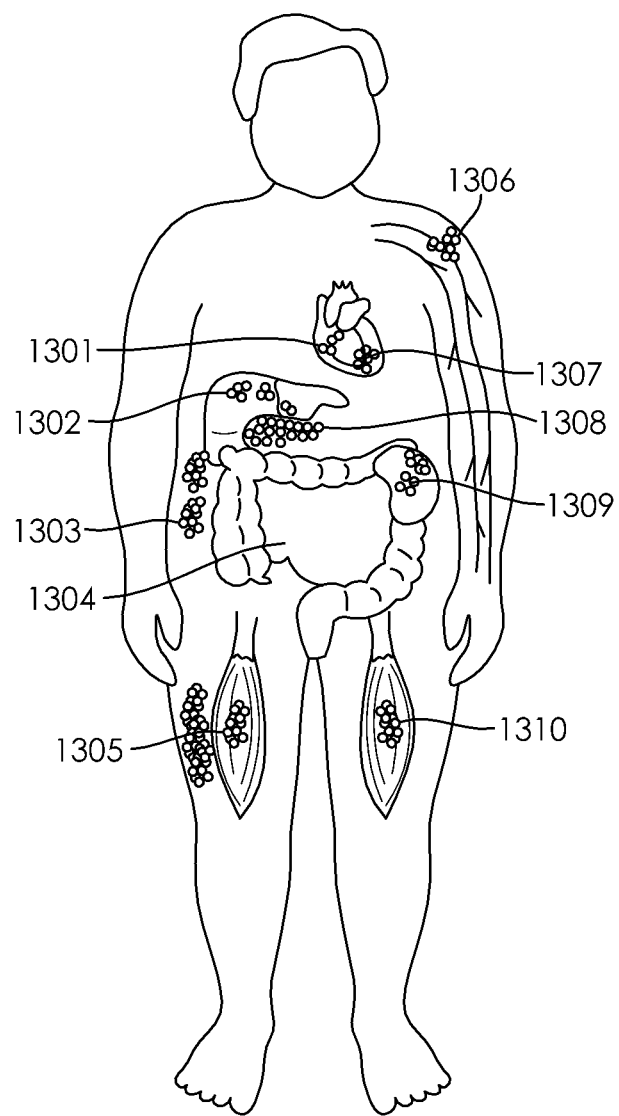
FIG. 12 shows various parts of a human body that can be imaged using the imaging system of FIG. 1 according to the method of FIG. 7.

Although in embodiments the object of interest is described as being the liver and the reference is described as being the kidney, those, skilled in the art will appreciate that thermoacoustic data may be obtained for other parts of the body. As shown in FIG. 12, various parts of the body that may be imaged using the above-described system and method include the epi/pericardial adipose tissue 1301, the liver 1302, subcutaneous adipose tissue 1303, visceral adipose tissue 1304, subcutaneous gluteal-femoral adipose tissue 1305, perivascular adipose tissue 1306, myocardial fat 1307, pancreas fat 1308, renal sinus fat 1309, and muscle fat 1310.

In another embodiment, the space enclosed by the insert 202, backplane 204 and the window 240 may be partially or fully-filled with material that conducts RF energy pulses such as for example a liquid, gel, ceramic or putty. As will be appreciated, in this embodiment, the material partially or fully filling the space may be heated or cooled thereby increasing or decreasing the temperature within the insert 202. As such, the frequency of the RF energy pulses may be adjusted.

Although embodiments have been described above with reference to the accompanying drawings, those of skill in the art will appreciate that variations and modifications may be made without departing from the scope thereof as defined by the appended claims.

What is claimed is:

1. A method for enhancing radio frequency energy delivery to a tissue region of interest, the method comprising:
   (i) emitting with a radio frequency (RF) applicator comprising a waveguide, one or more RF energy pulses into the tissue region of interest, the tissue region of interest comprising an object of interest and at least one reference that are separated by at least one boundary, wherein the boundary is at a location between at least two different types of tissue selected from a group consisting of muscle tissue, fat tissue, blood vessel tissue, liver tissue, and kidney tissue;
   (ii) detecting with an acoustic receiver, at least one bipolar acoustic signal generated in the tissue region of interest in response to the emitted one or more RF energy pulses and processing the at least one bipolar acoustic signal to determine a peak-to-peak amplitude thereof;
   (iii) tuning the RF applicator based on the determined peak-to-peak amplitude by at least one of (a) selectively adjusting an extent to which at least one tuning element extends into the waveguide thereby to alter an impedance of the waveguide, and (b) adjusting a temperature within the waveguide, the tuning selected to maximize a peak-to-peak amplitude of bipolar acoustic signals generated in the tissue region of interest in response to RF energy pulses emitted by the tuned RF applicator; and
   (iv) emitting with the tuned RF applicator, one or more RF energy pulses into the tissue region of interest.

2. The method of claim 1, further comprising performing thermoacoustic imaging of the tissue region of interest using the tuned RF applicator.

3. The method of claim 2, further comprising determining one or more parameters of the object of interest from the thermoacoustic imaging.

4. The method of claim 3, wherein the one or more parameters of the object of interest are at least one of fractional fat content and temperature.

5. The method of claim 1, wherein the tuning further comprises at least one of:
   adjusting a distance between the RF applicator and the tissue region of interest; and
   adjusting a volume of the waveguide of the RF applicator.

6. A system for enhancing radio frequency energy delivery to a tissue region of interest comprising an object of interest and at least one reference that are separated by at least one boundary, the system comprising:

a thermoacoustic imaging system comprising a tunable radio frequency (RF) applicator which includes a waveguide configured to emit RF energy pulses into the tissue region of interest and heat tissue therein, at least one tuning element selectively moveable into and out of the waveguide to adjust an impedance of the RF applicator, and an acoustic receiver configured to receive bipolar acoustic signals generated in response to heating of tissue in the tissue region of interest, wherein the bipolar acoustic signals are generated in the tissue region of interest at a boundary between at least two different types of tissue selected from a group consisting of muscle tissue, fat tissue, blood vessel tissue, liver tissue, and kidney tissue; and one or more processors configured to:
  process received bipolar acoustic signals during calibration of the RF applicator to determine a tuning setting for the RF applicator that yields, in response to RF energy pulses emitted by the RF applicator tuned by adjusting the extent to which the at least one tuning element extends into the waveguide in accordance with the tuning setting, generation of bipolar acoustic signals with maximum peak-to-peak amplitudes in the tissue region of interest.

7. The system of claim 6, wherein the one or more processors are further configured to:
  process bipolar acoustic signals received by the acoustic receiver with maximum peak-to-peak amplitudes to determine one or more parameters of the object of interest.

8. The system of claim 6, wherein the one or more parameters of the object of interest are at least one of fractional fat content and temperature.

9. The system of claim 6, wherein the tuning setting further comprises a distance between the tunable RF applicator and the tissue region of interest.

10. The system of claim 6, wherein the tuning setting further comprises waveguide volume and wherein the waveguide of the tunable RF applicator comprises an adjustable volume.

11. The system of claim 6, wherein the tuning setting further comprises temperature and wherein the tunable RF applicator comprises at least one heating element on the waveguide that is energizable to alter a temperature within the waveguide of the tunable RF applicator.

12. The system of claim 6, wherein the at least one tuning element is at least one threaded rod threadably engaged with the waveguide and rotatable to adjust the extent to which the threaded rod extends into the waveguide.

13. A method for enhancing radio frequency energy delivery to a tissue region of interest, the method comprising:
  (i) emitting, using a radio frequency (RF) applicator comprising a waveguide, one or more RF energy pulses into the tissue region of interest, the tissue region of interest comprising an object of interest and at least one reference that are separated by at least one boundary;
  (ii) detecting, using an acoustic receiver, at least one bipolar acoustic signal generated in the tissue region of interest in response to the emitted one or more RF energy pulses and processing the at least one bipolar acoustic signal to determine a peak-to-peak amplitude thereof, wherein the at least one bipolar acoustic signal is generated at a boundary location between at least two different types of tissue selected from a group consisting of muscle tissue, fat tissue, blood vessel tissue, liver tissue, and kidney tissue;
  (iii) tuning the RF applicator to adjust a frequency of RF energy pulses emitted thereby, wherein the tuning comprises at least one of (a) selectively adjusting an extent to which at least one tuning element extends into the waveguide thereby to alter an impedance of the waveguide, and (b) adjusting a temperature within the waveguide;
  (iv) emitting, using the tuned RF applicator, one or more RF energy pulses at the adjusted frequency into the tissue region of interest;
  (v) detecting, using the acoustic receiver, at least one further bipolar acoustic signal generated in the tissue region of interest in response to the emitted one or more RF energy pulses at the adjusted frequency emitted by the processing the at least one further bipolar acoustic signal to determine a peak-to-peak amplitude thereof, wherein the at least one further bipolar acoustic signal is generated at the boundary location;
  (vi) comparing the peak-to-peak amplitude at step (v) with a previously determined peak-to-peak amplitude; and
  (vii) repeating steps (iii), (iv) and (v) until the peak-to-peak amplitude of the at least one further bipolar acoustic signal determined at step (v) is maximized.

14. A method for enhancing delivery of radio frequency energy by a thermoacoustic imaging system to a tissue region of interest, the method comprising:
  (i) emitting with a radio frequency (RF) applicator of the thermoacoustic imaging system, one or more RF energy pulses into the tissue region of interest, the tissue region of interest comprising tissue of interest and reference tissue that are separated by a boundary, wherein the boundary is at a location between at least two different types of tissue selected from a group consisting of muscle tissue, fat tissue, blood vessel tissue, liver tissue, and kidney tissue;
  (ii) detecting with an acoustic receiver of the thermoacoustic imaging system, at least one bipolar acoustic signal generated in the tissue region of interest in response to the emitted one or more RF energy pulses and processing the at least one bipolar acoustic signal to determine a peak-to-peak amplitude thereof;
  (iii) tuning the RF applicator based on the determined peak-to-peak amplitude to adjust the frequency of RF energy pulses emitted thereby, the frequency being selected to maximize a peak-to-peak amplitude of bipolar acoustic signals generated in the tissue region of interest in response to RF energy pulses emitted by the tuned RF applicator, wherein the tuning comprises at least one of (a) selectively adjusting an extent to which at least one tuning element extends into the waveguide thereby to alter an impedance of the waveguide, and (b) adjusting a temperature within the waveguide; and
  (iv) emitting with the tuned RF applicator, one or more RF energy pulses at the adjusted frequency into the tissue region of interest.

15. The method of claim 14, further comprising performing thermoacoustic imaging of the tissue region of interest using the tuned RF applicator.

16. The method of claim 15, further comprising determining one or more parameters of the tissue of interest from the thermoacoustic imaging.

17. The method of claim 16, wherein the one or more parameters of the tissue of interest are at least one of fractional fat content and temperature.

* * * * *